(12) United States Patent
Mishra et al.

(10) Patent No.: US 11,341,462 B1
(45) Date of Patent: May 24, 2022

(54) GRAPHICAL USER INTERFACE FOR GENERATING A RECURRING APPOINTMENT REPORT BASED UPON USER INPUT

(71) Applicant: Allscripts Software, LLC, Raleigh, NC (US)

(72) Inventors: Amita Mishra, Burlington, MA (US); Lisa Gillis, Burlington, MA (US)

(73) Assignee: ALLSCRIPTS SOFTWARE LLC, Raleigh, NC (US)

( * ) Notice: Subject to any disclaimer, the term of this patent is extended or adjusted under 35 U.S.C. 154(b) by 258 days.

(21) Appl. No.: 16/273,086

(22) Filed: Feb. 11, 2019

(51) Int. Cl.
G06Q 10/10 (2012.01)
G06F 3/0482 (2013.01)
G06F 3/04842 (2022.01)
G06Q 10/06 (2012.01)
G16H 10/00 (2018.01)

(52) U.S. Cl.
CPC ....... *G06Q 10/1095* (2013.01); *G06F 3/0482* (2013.01); *G06F 3/04842* (2013.01); *G06Q 10/06314* (2013.01); *G16H 10/00* (2018.01)

(58) Field of Classification Search
USPC ...................................................... 705/7.19
See application file for complete search history.

(56) References Cited

U.S. PATENT DOCUMENTS

| | | |
|---|---|---|
| 6,272,074 B1 | 8/2001 | Winner |
| 7,149,810 B1 | 12/2006 | Miller et al. |
| 7,693,736 B1 * | 4/2010 | Chu ................... G06Q 10/1095 705/7.19 |
| 8,577,959 B2 * | 11/2013 | Pandey ................ G06Q 10/109 709/203 |
| 10,832,224 B2 * | 11/2020 | Palavalli .......... G06Q 10/06314 |
| 2006/0149609 A1 * | 7/2006 | Stenerson ............ G06Q 10/109 705/7.24 |
| 2007/0168892 A1 * | 7/2007 | Brush ................... G06Q 10/109 715/751 |
| 2008/0195455 A1 | 8/2008 | May et al. |
| 2009/0307044 A1 * | 12/2009 | Chakra ................ G06Q 10/109 705/7.18 |
| 2010/0036676 A1 * | 2/2010 | Safdi ...................... G06Q 10/10 705/2 |
| 2010/0070297 A1 * | 3/2010 | Kharraz Tavakol ... G06Q 10/10 705/2 |
| 2010/0191563 A1 * | 7/2010 | Schlaifer ................ G16H 40/20 705/7.36 |
| 2010/0191566 A1 * | 7/2010 | Loring ................. G06Q 10/109 705/7.19 |

(Continued)

OTHER PUBLICATIONS

Vanden Berghe, Greet. "An advanced model and novel metaheuristic solution methods to personnel scheduling in healthcare." (2002) (Year: 2002).*

Primary Examiner — Susanna M. Diaz
Assistant Examiner — Darlene Garcia-Guerra
(74) Attorney, Agent, or Firm — Calfee, Halter & Griswold LLP (57) ABSTRACT

Described herein are various technologies pertaining to generating and/or updating a schedule such that the schedule includes a recurring appointment. The schedule is generated and/or updated based upon inputs received at a GUI that includes a matrix of checkboxes, such that the schedule is able to be constructed to include a recurring appointment for an Nth occurrence of a selected day in each month.

20 Claims, 5 Drawing Sheets

(56) References Cited

U.S. PATENT DOCUMENTS

| | | | | |
|---|---|---|---|---|
| 2011/0054976 A1* | 3/2011 | Adler | ................... | G06Q 10/109 |
| | | | | 705/7.18 |
| 2011/0246226 A1* | 10/2011 | Green, III | ............... | G16H 40/20 |
| | | | | 705/2 |
| 2013/0010575 A1* | 1/2013 | He | ....................... | G06Q 10/109 |
| | | | | 368/10 |
| 2014/0039906 A1 | 2/2014 | Wang et al. | | |
| 2014/0136259 A1* | 5/2014 | Kinsey, II | .......... | G06Q 10/1095 |
| | | | | 705/7.16 |
| 2014/0278535 A1* | 9/2014 | Romeo | .............. | G06Q 10/1095 |
| | | | | 705/3 |
| 2014/0310045 A1* | 10/2014 | Meltzer | .............. | G06Q 10/1095 |
| | | | | 705/7.19 |
| 2014/0365261 A1* | 12/2014 | Liu | ................ | G06Q 10/063116 |
| | | | | 705/7.19 |
| 2015/0112738 A1* | 4/2015 | Marinaro | ............... | G06Q 10/02 |
| | | | | 705/5 |
| 2015/0149203 A1* | 5/2015 | Csurka | ............... | G06Q 10/1095 |
| | | | | 705/3 |
| 2016/0048809 A1* | 2/2016 | Arbabian | ........... | G06Q 10/1095 |
| | | | | 705/7.19 |
| 2016/0328522 A1* | 11/2016 | Howley | ................. | G16H 10/60 |
| 2017/0329922 A1* | 11/2017 | Eberting | ................ | G06Q 20/40 |
| 2018/0012195 A1* | 1/2018 | Nagaraj | ............ | G06Q 10/1095 |
| 2019/0237203 A1* | 8/2019 | Schwabl | ............ | G06Q 10/1095 |
| 2020/0118045 A1* | 4/2020 | Chung | ............... | G06Q 10/1095 |

* cited by examiner

GRAPHICAL USER INTERFACE FOR GENERATING A RECURRING APPOINTMENT REPORT BASED UPON USER INPUT

BACKGROUND

Electronic health record applications (EHRs) are computer-executable applications that are configured to assist healthcare workers with providing care to patients. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve data from a patient record maintained by an EHR to relatively quickly ascertain problems being experienced by the patient, medications currently being taken by the patient, and so forth.

A conventional EHR often includes modules that are configured to perform certain functions of the EHR. For instance, a conventional EHR may include a module for obtaining and displaying radiographs, a module for transmitting prescriptions to a pharmacy, a module for billing insurance companies, a module for scheduling (which can include scheduling time, reserving rooms, etc.), amongst other modules. Conventional EHRs, however, are currently ill-equipped to assist healthcare workers with scheduling certain types of recurring blocks of time. In a non-limiting example, conventional EHRs are currently not equipped to allow for the scheduling of irregular block schedules. Thus, for instance, while a conventional scheduling module is well-suited to schedule recurrent blocks on a daily, weekly, or monthly basis, the conventional scheduling module is ill-equipped to assist with scheduling more irregular recurrent blocks.

Healthcare workers (e.g., physicians, hospital administrators, etc.) use scheduling blocks to schedule recurring appointments to create predictable schedules in shared medical spaces as well as in their own offices. For example, operating rooms present logistical difficulties for use such as availability, doctor preferences, room supplies, etc. Therefore, scheduling time and resources in advance, wherein specific doctors work in certain rooms at certain times on certain days, facilitates ensuring that resources are allocated properly when providing care to patients. Known recurrence patterns help increase efficiency as operating room employees are able to follow a predictable schedule. However, existing solutions are not well-suited to assist with more complex recurrent scheduling. For instance, a first surgeon may have her operating room day be every second Tuesday and every fourth Wednesday of a month, while a second surgeon may have his operating room day be every first Thursday, every third Monday and every fifth Friday of a month. Conventional scheduling tools require a user to manually identify each date and time individually, which is burdensome and error-prone, and not well-suited for scheduling very far in advance.

SUMMARY

The following is a brief summary of subject matter that is described in greater detail herein. This summary is not intended to be limiting as to the scope of the claims.

Described herein are various technologies pertaining to generating a recurring monthly block schedule based on input received from a graphical user interface (GUI). More specifically, a computer-executable application is in communication with an electronic health record application (EHR), wherein the computer-executable application is configured to receive input by way of its GUI from a user, wherein the input comprises scheduling information relating to a healthcare worker providing care to a patient. The computer-executable application provides a user with the ability to customize a schedule for a healthcare worker or healthcare facility to aid in efficient allocation of resources such as operating rooms. The scheduling application can optionally automatically release a scheduling block not being used by a healthcare worker to allow other healthcare workers to pick up that scheduling block. With more particularity, an EHR can have, as a module, the computer-executable scheduling application. In another embodiment, the scheduling application may be separate from the EHR and may acquire clinical data from a suitable data source (which may be the EHR, a health information exchange (HIE), or the like).

In an exemplary embodiment, the scheduling application can be a distributed application that includes client-side software (a client scheduling application) and server-side software (a server scheduling application) that interacts with the client scheduling application. Similarly, the EHR can be a distributed application that includes client-side software (a client EHR) and server-side software (a server EHR) that interacts with the client EHR. In such an embodiment, a client computing device executes both the client scheduling application and the client EHR, while a server computing device (in network communication with the client computing device) executes the server scheduling application and the server EHR. The client scheduling application receives an identifier for the healthcare worker and an indication that an appointment is desired to be scheduled for the healthcare worker at dates and locations. The identifier may be the name of the healthcare worker, an identifying employee number for the healthcare worker, etc. The client scheduling application transmits the identifier to the server scheduling application, and the server scheduling application, in response to receipt of the identifier for the healthcare worker, searches scheduling data maintained by the EHR and/or the server scheduling application for scheduling information assigned to the healthcare worker, and further searches the scheduling data to ascertain whether the desired date(s) and location(s) for the appointment are available. In a non-limiting example, a healthcare worker may wish to schedule time in an operating room at a particular time every first, third, and fifth Monday of each month. Presuming that the operating room is available on those dates at the particular time, the server scheduling application blocks off those dates and times for that healthcare worker, wherein subsequently this schedule can be updated with additional times, dates, or locations (i.e. operating room, office room, etc.) regarding the healthcare worker's schedule from scheduling data maintained by the server EHR and/or updated with information solicited from the healthcare worker. If any appointment time in the recurring scheduling block is not going to be used, the scheduling application will automatically release the time.

The client scheduling application is configured to receive input by way of a GUI of the client scheduling application, wherein the GUI is configured to facilitate defining a schedule of appointments for a healthcare worker; as indicated above, responsive to the client scheduling application receiving input by way of the GUI, the client scheduling application transmits the input to the server scheduling application, which updates scheduling data in a database based upon such input. In an example, the server scheduling application can be a module of the EHR, and accordingly the database can be maintained by the EHR. Hence, the scheduling application can acquire scheduling data directly from the EHR and can update the scheduling data of the EHR. The scheduling data can include scheduling information about a facility (e.g., operating room, examination room, etc.) or healthcare group (e.g., general surgery, cardiac units, etc.) as well as clinical data about a patient being seen by the healthcare worker during a scheduling block to provide an overview of the healthcare worker's day. The clinical data can include any suitable data that may be maintained by the EHR, including but not limited to family history information, symptoms reported by the patient, symptoms observed by a clinician, and so forth. The scheduling data can include data that is indicative of schedule of a healthcare worker, schedule of a facility, etc.

When a healthcare worker requests scheduling data by way of the GUI of the client scheduling application, the client scheduling application transmits the request to the server scheduling application, and the server scheduling application generates a schedule for the healthcare worker (or a facility), wherein the schedule comprises a schedule of appoints, and further wherein a patient for each appointment is identified as well as the location of the appointment (e.g., office, operating room, imaging center, etc.). Optionally, the server scheduling application generates a report, wherein the report is configured for use in compiling a schedule for the healthcare worker or healthcare facility, and further wherein the report comprises an identification of appointment type (e.g. post-op exam, appendectomy, colonoscopy, etc.). For example, the server scheduling application can generate the report based upon content of the clinical data and scheduling data, such that the scheduling application need not request additional information from the healthcare worker operating the client computing device when the database of the EHR already comprises such data relating to the desired schedule. The server scheduling application then transmits the schedule and optionally the report to the client scheduling application, whereupon the schedule and the report can be presented by way of the GUI of the client scheduling application on a display. The healthcare worker can then interact with the GUI of the client scheduling application to alter scheduled times (e.g. add a new appointment time, delete an appointment time, block of certain dates, etc.), change the recurring range of appointments, change the range of dates displayed, or add or remove healthcare workers or healthcare facilities to/from the system.

The scheduling application described herein provides various advantages over conventional EHRs and approaches for generating schedules. The client scheduling application provides a GUI that is configured to assist healthcare workers with scheduling irregular, but recurring scheduling blocks. Therefore, rather than requiring the healthcare worker to manually enter each appointment over a relatively long window of time (e.g. several months), the GUI is configured to define irregular but recurring scheduling blocks over a range of time defined by the healthcare worker based upon a relatively small number of inputs.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to graphical user interfaces that are configured to present scheduling options to a healthcare worker are described herein. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Described herein are various technologies pertaining to generating and/or updating a schedule, and further pertaining to generating a schedule with irregular but recurring appointments, wherein times of appointments are based upon input received by way of a graphical user interface (GUI) of a scheduling application. Optionally, the schedule may be made based upon input from a hospital administrator, a clinician, or other authorized hospital employee. In a healthcare setting, specifically a hospital, efficient allocation of resources is essential for ensuring patients are receiving timely and proper healthcare. For example, operating rooms are highly specialized rooms within a hospital setting. Not every operating room is outfitted with the same technology; therefore, not every operating room is appropriate for every surgery performed at a hospital. In a non-limiting example, a hospital may have only one operating room that is outfitted for cardiac surgeries; however, there are multiple cardiac surgeons who each need access to the operating room, thereby putting the room in high demand and increasing the probability of a schedule including a conflict. Enabling predictable, recurring (but irregular) block scheduling for each of these surgeons, wherein unused appointment blocks in a surgeon's schedule are automatically released to allow other surgeons to use the operating room during that time, enhances the efficient use of hospital resources.

Conventional scheduling assistance tools, however, are not configured to allow this type of scheduling, and are further not configured to schedule recurring but irregular appointments or to automatically release unfilled appointment blocks in the schedule. Instead, conventional scheduling assistance tools require a healthcare worker to manually schedule each appointment block separately and, in the event the healthcare worker does not schedule an appointment during the blocked time, the healthcare worker would be responsible for releasing the time to allow other healthcare workers to use the operating room, which a healthcare worker may not remember to do due to his or her very busy schedule.

Figure 1:
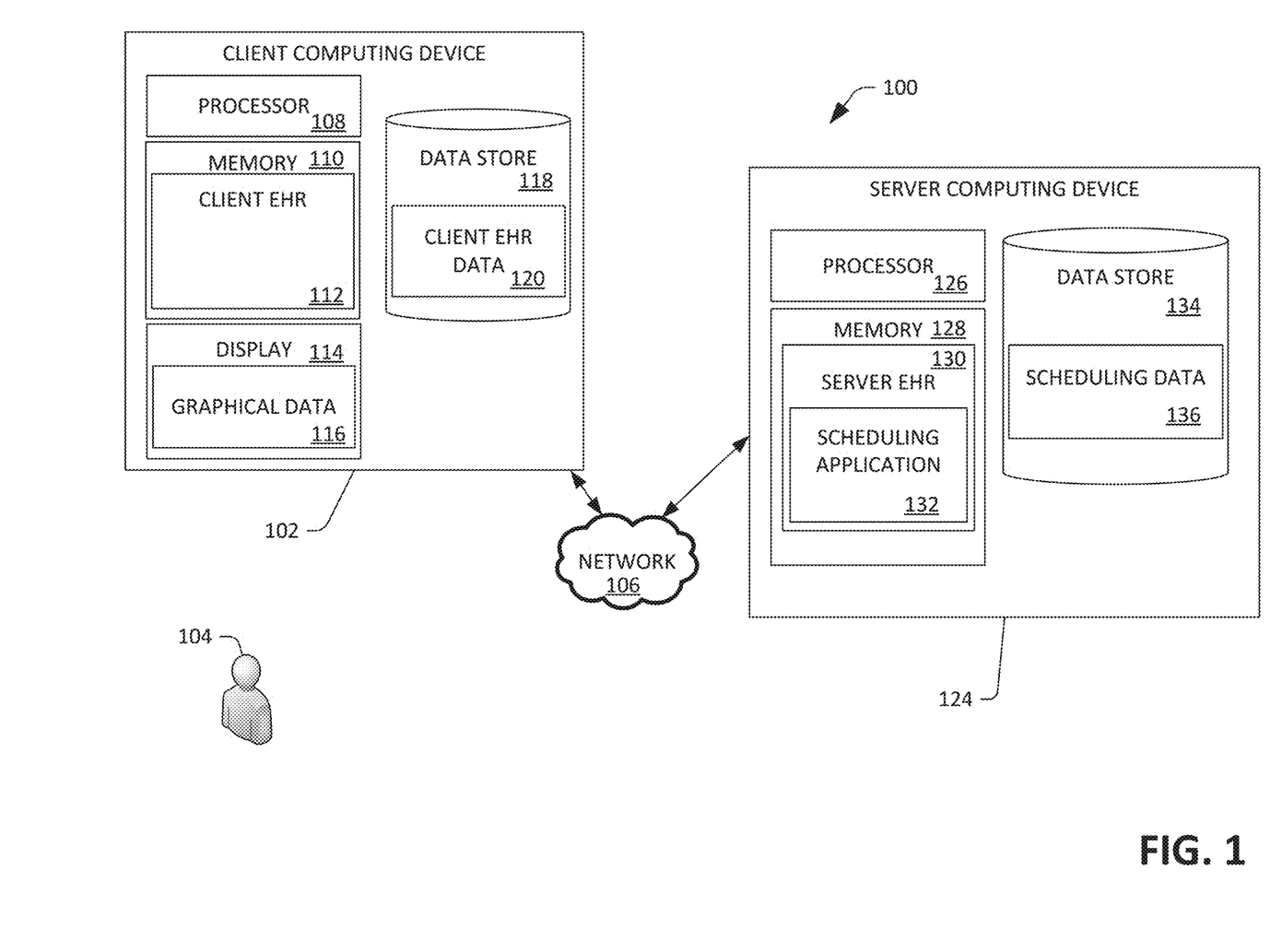
FIG. 1 is a functional block diagram of an exemplary computing system that facilitates generating a block schedule.

With reference now to FIG. 1, an exemplary system 100 that facilitates generating a schedule for a healthcare worker based on inputs received by way of a GUI of a scheduling application of a client EHR is illustrated. The system 100 includes a client computing device 102 that is operated by a healthcare worker 104 (e.g., a physician, administrator, etc.). The client computing device 102 may be any suitable type of computing device, including a desktop computing device, a laptop computing device, a tablet computing device, a mobile telephone, etc.

The client computing device 102 comprises a processor 108, memory 110, a display 114, and a data store 118. The memory 110 stores instructions that are executed by the processor 108. More specifically, the memory 110 has loaded therein a client EHR 112. The display 114 is configured to display graphical data 116 that is presented to the healthcare worker 104, for example, by way of a graphical user interface (GUI) of the client EHR 112, wherein the graphical data 116 comprises features that facilitate presenting, generating, and updating a schedule for a healthcare worker. As will be described in greater detail below, the features of the GUI can be well-suited for generating a schedule that includes recurrent but irregular appointments, wherein, based on input received by way of the GUI, an appointment for a healthcare worker can be set to recur in accordance with a pattern defined by the healthcare worker 104 by way of the GUI. In another example, the schedule can comprise scheduling information for a particular room (e.g. operating room, examination room, medical imaging room, etc.). For instance, the graphical data 116 can comprise input options corresponding to monthly recurrence, wherein an appointment can be defined to recur every month, every two months, every three months, etc. In another example, the graphical data 116 can comprise input options corresponding to a defined recurrence range. For instance, the schedule for a month can be set to recur from Feb. 9, 2018 through Nov. 9, 2018.

The data store 118 comprises client EHR data 120, which can include scheduling data about a healthcare worker 104 and clinical data pertaining to patients on the healthcare worker's schedule. The graphical data 116 shown on the display 114 can also include portions of the client EHR data 120 or data generated based upon the client EHR data 120.

The system 100 further includes a server computing device 124 that is in communication with the client computing device 102 by way of a network 106, such as the Internet or an intranet. The server computing device 124 includes a processor 126 and memory 128, wherein the memory 128 has a server EHR 130 loaded therein. The server EHR 130 is configured to perform a variety of tasks related to patient care in a healthcare facility, including patient intake, patient record creation and maintenance, etc. The server computing device 124 further includes a data store 134 that comprises scheduling data 136, which may, for example be stored in a database separate from clinical data. The scheduling data 136 is maintained by the server EHR 130, wherein the scheduling data 136 can include schedules for healthcare workers, schedules for facilities (e.g. operating rooms), schedules for groups of healthcare workers (e.g., a surgery team), etc.

In the exemplary system 100, the server EHR 130 includes a scheduling application 132, which can be a module of the server EHR 130. Summarily, the scheduling application 132 is configured to receive an identifier for a healthcare worker or a facility. Responsive to receiving the identifier, the scheduling application 132 is configured to retrieve, from the scheduling data 136, scheduling information for the healthcare worker or facility, and is further configured to generate and output a report comprising scheduled appointments for the healthcare worker or the facility over a range of time (and optionally related information). The scheduling application 132 generates the report based upon the scheduling information for the healthcare worker or facility. The scheduling information for the healthcare worker can include, but is not limited to, office appointments of the healthcare worker, administration appointments of the healthcare worker, vacation time of the healthcare worker, operating room blocks, scope blocks, and so forth. The scheduling information about the facility can include, but is not limited to, operating blocks indexed to healthcare workers, available time(s) for the facility, operating blocks indexed to uses (e.g. appendectomies, hysterectomies, cardiovascular operations, etc.), etc.

Exemplary operation of the system 100 is now set forth. The client EHR 112 executing on the client computing device 102 receives user credentials (e.g., username and password) from the healthcare worker 104, and the client EHR 112 causes the client computing device 102 to transmit the user credentials to the server computing device 124. The server EHR 130 authenticates the healthcare worker 104, such that the healthcare worker 104 is able to access data maintained by the server EHR 130 by way of the client EHR 112. Subsequent to the server EHR 130 authenticating the user credentials of the healthcare worker 104, the client computing device 102 receives, from the healthcare worker 104, an identifier for a subject and an indication that a schedule is to be generated and/or updated for the identified subject. The subject can be a healthcare worker, a healthcare group, or a facility (e.g., an operating room, an MRI machine, an X-ray machine, etc.), and the identifier of the subject uniquely identifies the subject. The identifier for the subject and the indication that the schedule is to be generated and/or updated for the subject can be received based upon a single user interaction with the client EHR 112 or multiple user interactions with the client EHR 112. Responsive to receipt of the subject identifier and the indication that the schedule for the subject is to be generated and/or updated, the client EHR 112 transmits the subject identifier to the server EHR 130 as well as the indication that the schedule is to be generated and/or updated for the subject.

The scheduling application 132, responsive to receiving the indication that to the schedule is to be generated and/or updated for the subject, searches the scheduling data 136 for scheduling information for the subject. For instance, the scheduling application 132 can retrieve existing scheduling information for a healthcare worker from the scheduling data 136 based upon the received identifier for the subject (i.e., the healthcare worker). The scheduling application 132 can construct a scheduling report for the subject based upon the scheduling information about the subject in the scheduling data 136. For instance, if the scheduling information about a healthcare worker indicates that Mondays and Wednesdays are spent in the healthcare worker's office meeting patients and Tuesdays and Thursdays are spent in the operating room performing medical procedures and Fridays are spent performing colonoscopies, the scheduling application 132 can generate a report indicating those times with patients and times identified therein as found in the scheduling data 136.

The scheduling application 132 transmits the scheduling report to the client EHR 112 executing on the client computing device 102, whereupon the client EHR 112 causes the scheduling report to be displayed on the display 114 of the client computing device 102 in the GUI of the client EHR 112. The healthcare worker 104 can then interact with, customize, or augment the resulting scheduling report in connection with generating and/or updating a schedule for the subject. In particular, the healthcare worker 104 can create and/or update a schedule using variable scheduling blocks, wherein the healthcare worker 104 can define block scheduling for the identified subject by way of the client EHR 112. A variable scheduling block is one where an Nth occurrence of a specified day of two or more months is reserved in the schedule for the subject. For example, a schedule for a general surgeon may include a reservation of an operating room each second Tuesday and each fourth Wednesday of each month. In another example, a schedule for another surgeon may include a reservation of the operating room day for each first Thursday, each third Monday, and each fifth Friday of a month. In yet another example, a schedule for an operating room may include a reservation for cardiovascular surgeons each second, third and fifth Wednesday of each month and may further include a reservation for general surgeons each first and fourth Wednesday of each month.

The scheduling application 132 can update the scheduling data 136 based upon changes made to the scheduling report by way of the GUI of the client EHR 112. For example, if the subject is the healthcare worker, and the healthcare worker updates the scheduling report to indicate that the healthcare worker has a vacation scheduled for two weeks, the scheduling application 132 can release reservations within that two week period while retaining the reservations before and after the two week period (thereby allowing the operating room to be scheduled by others during the times during the two-week period that would the operating room would be reserved for the healthcare worker. Thus, in addition to updating the schedule of the healthcare worker, the scheduling application 132 can generate an updated schedule for the operating room.

In a more specific example, the scheduling application 132 can allow for scheduling of variable scheduling blocks (e.g., that is not possible using conventional scheduling tools. For instance, the scheduling application can reserve time in a room for each fifth occurrence of a day in a month. For example, the scheduling application 132 can generate a schedule, wherein a healthcare worker is scheduled for time in an operating room the first, third, and fifth Tuesdays in each month. The hospital administrators and/or schedulers can then use the information presented in the scheduling report to aid in identifying peak traffic times, production, as well as increase the number of patients to whom care can be provided by allocating resources effectively and efficiently.

The scheduling application 132 exhibits various advantages over conventional scheduling software tools. As noted above, the scheduling application 132 is able to generate schedules that include variable scheduling blocks (e.g., reserving a room at a certain time on an Nth occurrence of a specified day of one or more months), while conventional scheduling software tools are unable to accommodate variable block scheduling. Scheduling variable blocks of time, as described above, is particularly well-suited for use in the medical field, where healthcare workers often wish to schedule in this manner. While conventional scheduling software tools allow a user to block schedule identical days (e.g., every Monday in a month, every Friday in a month, etc.), conventional scheduling software does not allow for variable block scheduling (e.g., the first Monday of every month, the second Tuesday of every month, and the third Friday of every month). Additionally, conventional scheduling software tools do not allow for the automatic inclusion of a fifth occurrence of a day in a month, which can result in wasted treatment times. The scheduling application 132 allows a user to specify the inclusion of a fifth occurrence of every month every time it occurs in a calendar year. Further, the scheduling application 132 can automatically release unused appointments in a scheduling block to facilitate more efficient use of hospital resources (unlike conventional scheduling software tools).

Figure 2:
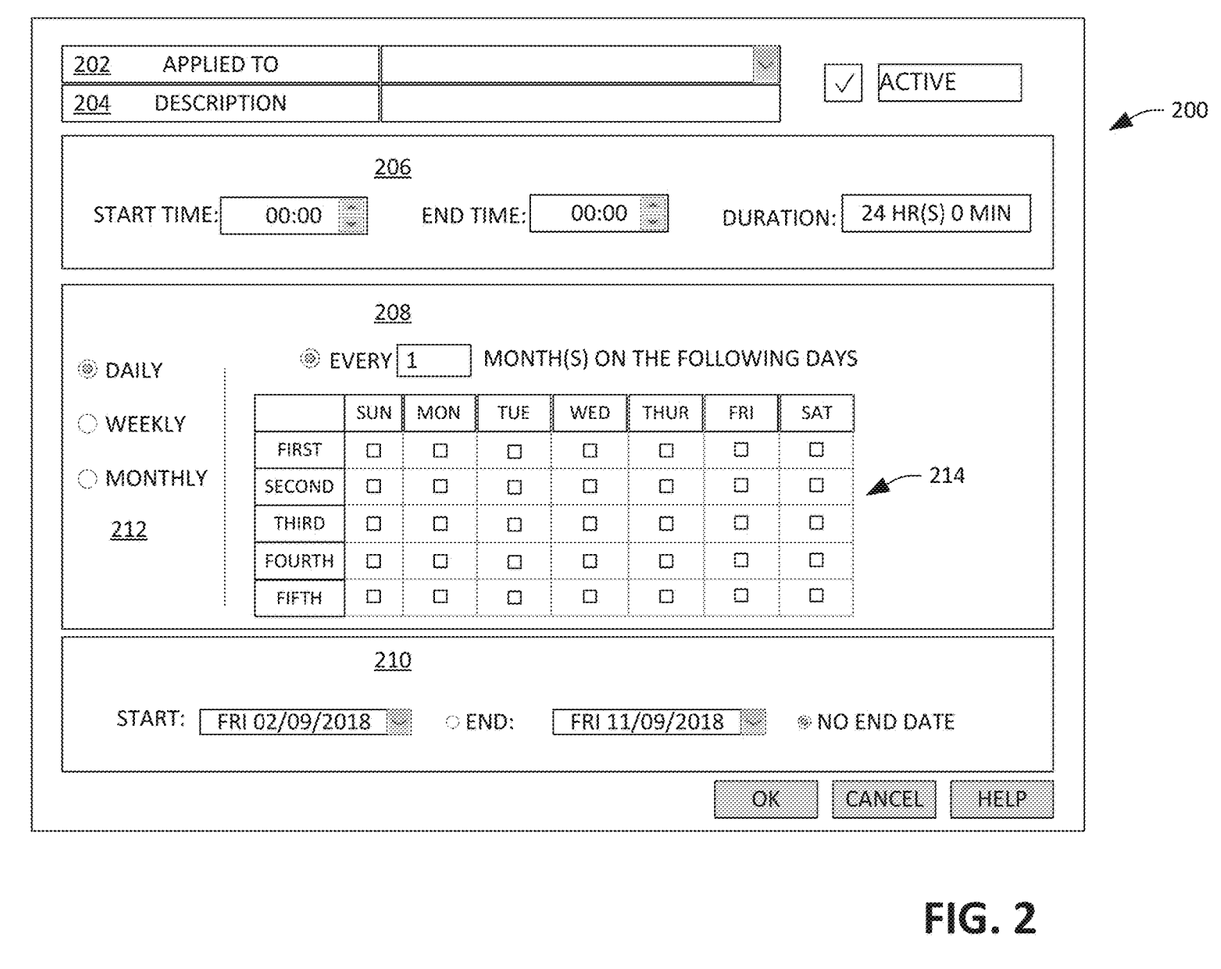
FIG. 2 depicts an exemplary graphical user interface (GUI) for a computer-executable application that is configured to generate a block schedule.

Now referring to FIG. 2, an exemplary graphical user interface (GUI) 200 presented to the healthcare worker 104 and/or the patient by the client EHR 112 is illustrated. The GUI 200 comprises a subject identifier field 202, description field 204, an appointment time field 206, a recurrence pattern field 208, and a range of recurrence field 210. The subject identifier field 202 can be configured to receive an identifier for a subject, such as a clinician identifier code, a clinician name, a room code, a room name, etc., wherein the subject identifier identifies a subject for whom a schedule is to be generated and/or updated. The description field 204 can be configured to receive a description for an appointment (or recurring appointment); for example, a type of procedure that occurs during the appointment. In the case of the schedule being for a facility (e.g., a room), the description field 204 can recite a description of the intended usage of the facility for an appointment or appointments, for example, the intended use of an operating room (e.g. appendectomies, open heart surgeries, etc.), an identify of a healthcare worker or group that is to be using the facility during the appointment or appointments, etc. The appointment time field 206 comprises fields that are configured to receive input that defines a start time for an appointment and an end time for the appointment. The appointment time field 206 can also comprise a field to display the total duration of the appointment based on the defined start and end time. For example, when the GUI 200 receives input from the healthcare worker 104 that an appointment is to start at 8:00 AM and end at 10:00 AM, the field 206 can be updated to indicate that the duration for the appointment is 2 hours, 0 minutes.

The recurrence pattern field 208 comprises a frequency field 212 and a customizable matrix field 214. The frequency field 212 comprises selectable options corresponding to the frequency of recurrence of the appointment that is being scheduled. In an embodiment illustrated in FIG. 2, the frequency field 212 comprises three options: daily, weekly, and monthly, wherein a separate selectable radio button corresponds to each option. For example, if the daily option of the frequency field 212 is selected in the GUI 200, and the appointment time field 206 indicates that the appointment is to occur between 8:00 AM to 10:00 AM, then the scheduling application 132 can generate/update a schedule for the subject such that an appointment occurring daily between 8:00 AM to 10:00 AM is scheduled for the subject in response to the user selecting an "OK" button in the GUI 200.

The customizable matrix field 214 is configured to receive input that allows for scheduling variable scheduling blocks, instead of the conventional frequencies in the frequency field 212. The customizable matrix 214 comprises a matrix of checkboxes, wherein the matrix comprises five rows, wherein each row corresponds to a week within a month, and seven columns, wherein each column corresponds to a day within a week. For example, returning to an example set forth above, if the healthcare worker 104 desired to be scheduled to perform appendectomies from 8:00 AM to 10:00 AM each first, third and fifth Monday in one or more months, and each second and fourth Tuesday in one or more months, the matrix 214 can receive input corresponding to those days in the form of selection of appropriate checkboxes in the matrix that correspond to those days. The customizable matrix field 214 is further configured to receive input that defines how often the recurrence pattern defined in the matrix is to be scheduled. For example, the GUI 200 can receive input that indicates that the recurrence pattern defined in the matrix is to recur every single month. Alternatively, the GUI 200 can receive input that indicates that the recurrence pattern defined in the matrix is to recur every other month, and so forth.

Finally, the range of recurrence field 210 comprises a first drop-down bar that can be interacted with to define the start time of the recurrence period, and a second drop down bar that can be interacted with to define the end of the recurrence period. Optionally, the GUI 200 can comprise a first selectable radio button next to the second drop down bar for the end of the recurrence period as well as a second selectable radio button next to an option reading "NO END DATE". For example, when the second selectable radio button next to the "NO END DATE" option is selected, the scheduling application 132 schedules the appointment on a recurring basis based on the definitions set in the recurrence pattern 208 field, as discussed above, without a defined end date. In an embodiment, the range of recurrence field 210 of the GUI receives input corresponding to a start date of the recurring appointment, for example, Friday, Feb. 9, 2018. The range of recurrence field 210 of the GUI receives input corresponding the selection of the first selectable radio button as well as input corresponding to an end date, for example, Friday, Nov. 9, 2018. In this embodiment, when the recurrence pattern defined in the recurrence pattern field indicates that recurring appointments are to start on Friday, Feb. 9, 2018 and continue until Friday, Nov. 9, 2018, the scheduling application 132 can generate a schedule that includes the recurring pattern of appointments that ceases on Nov. 9, 2018, unless the scheduling application 132 receives input that modifies the recurring appointments prior to Nov. 9, 2018. In an additional embodiment, the range of recurrence field 210 of the GUI receives input corresponding to a start date of the recurring appointment, for example, Friday, Feb. 9, 2018. The range of recurrence field 210 of the GUI receives input corresponding the selection of the second selectable radio button corresponding to the "NO END DATE" definition. In this embodiment, the recurrence pattern defined in the recurrence pattern field 208 would recur starting Friday, Feb. 9, 2018 and continue into perpetuity, or at least as far out as the scheduling application 132 allows, until input is provided to the scheduling application 132 indicating that the recurring appointment is to cease.

While the GUI 200 has been described as being a GUI generated by the client EHR 112, it is to be understood that the GUI 200 is well-suited for other applications, including but not limited to email applications, instant messaging applications, unified communications applications, and the like.

Figure 3:
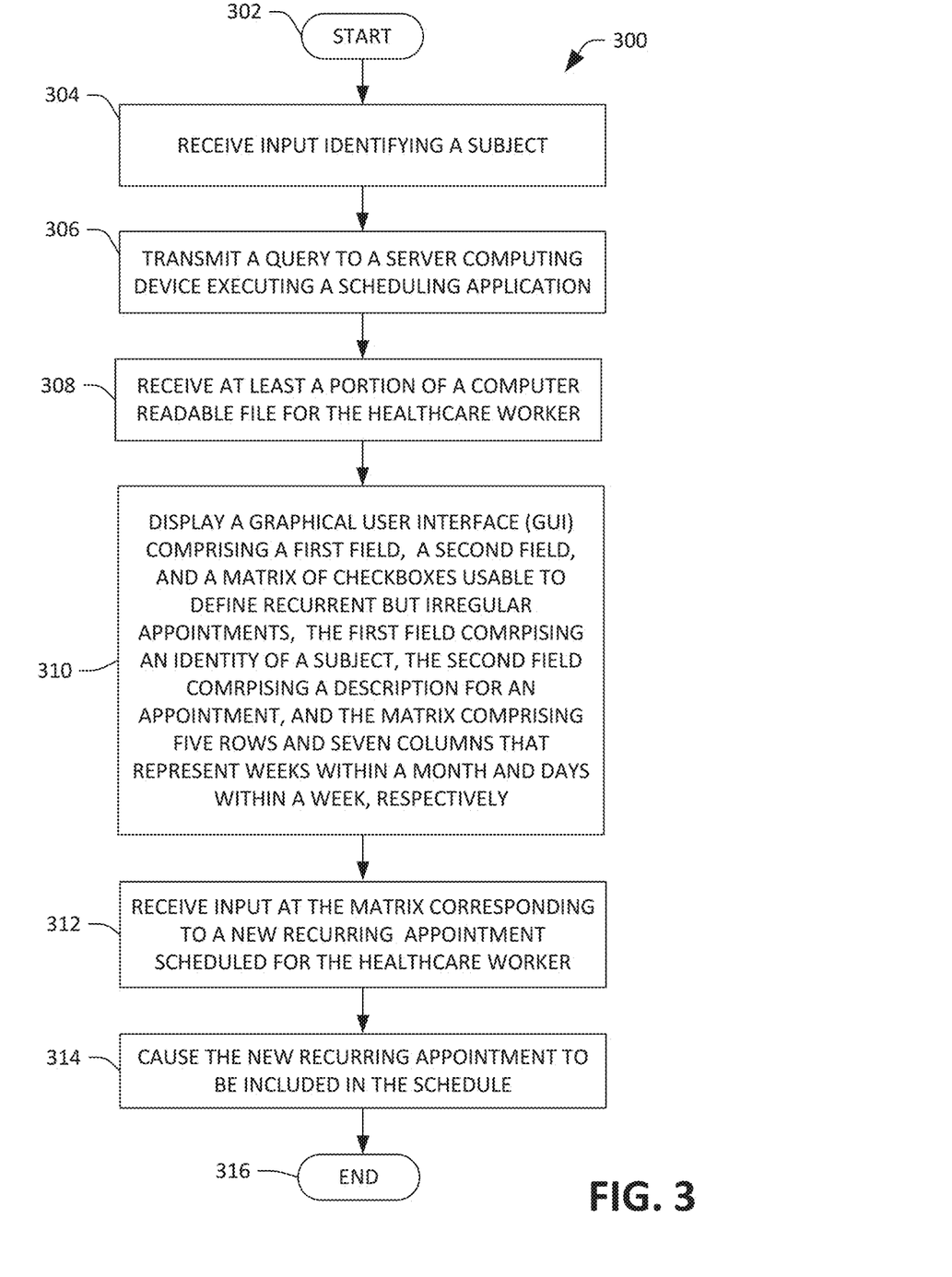
FIG. 3 is a flow diagram illustrating an exemplary methodology for generating a block schedule.
Figure 4:
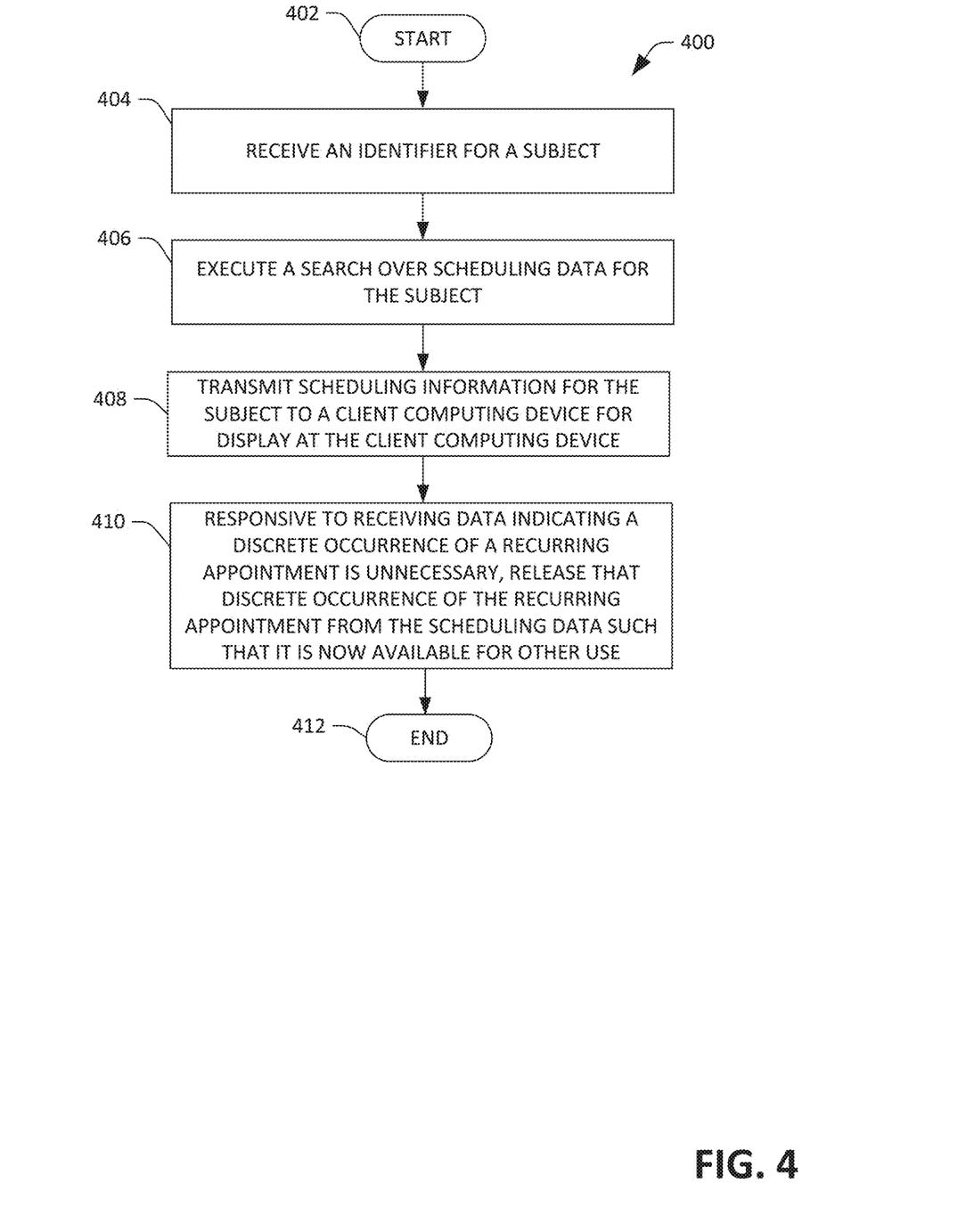
FIG. 4 is a flow diagram illustrating an exemplary methodology for generating a block schedule

FIGS. 3-4 illustrates exemplary methodologies relating to generating and/or updating a schedule through use of a computer-implemented scheduling application. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement the methodologies described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 3, a methodology 300 executed at a client computing device that facilitates generating and/or updating a schedule is illustrated. The methodology 300 begins at 302, and at 304 a subject identifier is received by way of a GUI of a client EHR executing on the client computing device from a user of the client computing device. At 306, a query is transmitted to a server computing device that executes a scheduling application, wherein the scheduling application searches for scheduling information about the subject based upon the query. This scheduling information can include existing appointments, vacation time, room assignments, and so forth. At 308, the client computing device receives scheduling information corresponding to the identified subject from the server computing device. At 310, an indication is received that a new appointment is to be scheduled for the subject, and responsive to receiving this indication, a GUI is presented on the display of the client computing device, wherein the GUI includes features that are configured to receive input pertaining to a new appointment (which may be a recurring appointment). The GUI comprises a first field and a second field, wherein the first field comprises the identity of the subject and the second field is configured to receive a description of the appointment. Additionally, the GUI comprises a matrix of check boxes that allow for the scheduling of recurrent, but irregular appointments. Specifically, the matrix comprises five rows, wherein each row represents a respective week within a month. The matrix additionally includes seven columns, wherein each column represents a respective day within a week. At 312, the GUI receives input corresponding to a new recurring appointment scheduled for the healthcare worker that was previously not stored in a database of the server computing device executing the scheduling application, wherein the recurrence pattern of the appointment is defined based upon user input to the matrix. At 314, the GUI is updated and the new recurring appointment is included in the subject's schedule. The methodology 300 concludes at 316.

Referring now to FIG. 4, a methodology 400 executed at a server computing device that facilitates generating and/or updating a schedule is illustrated. The methodology 400 begins at 402, and at 404 a subject identifier is received from a client computing device that is in network communication with the server computing device. At 406, a scheduling application executing on the server computing device searches over scheduling data stored in a database maintained by the server computing device for scheduling information about the healthcare worker. This scheduling information can include existing appointments, schedules, vacation time, room assignments, and so forth. At 408, the server computing device transmits the scheduling information about the healthcare worker to the client computing device. At 410, responsive to receiving data from the client computing device indicating that a discrete occurrence of a recurring appointment is unnecessary (e.g., a patient cancelled that appointment, no patient was ever scheduled during that time, a healthcare worker is ill, a healthcare worker is on vacation, etc.), updating the scheduling information to release the appointment time, thereby allowing that time to be used for another purpose (such as for another patient or for another healthcare worker). The server computing device then stores the updated scheduling information in the database. The methodology 400 concludes at 412.

Figure 5:
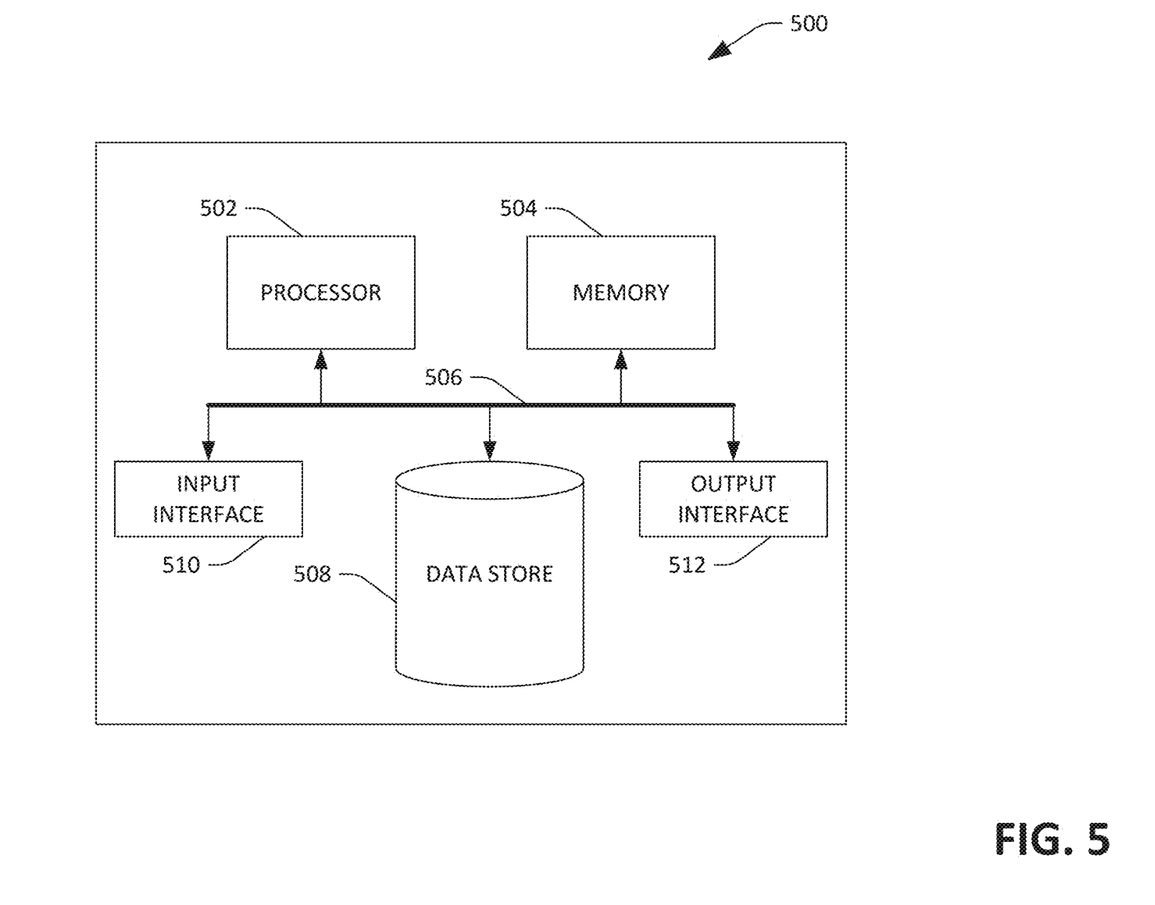
FIG. 5 is an exemplary computing system.

Referring now to FIG. 5, a high-level illustration of an exemplary computing device 500 that can be used in accordance with the systems and methodologies disclosed herein is illustrated. For instance, the computing device 500 may be used in a system that generates appointments on a healthcare worker's schedule based on user inputs. By way of another example, the computing device 500 can be used in a system that generates recurring appointments on a healthcare worker's schedule based on user inputs. The computing device 500 includes at least one processor 502 that executes instructions that are stored in a memory 504. The instructions may be, for instance, instructions for implementing functionality described as being carried out by one or more components discussed above or instructions for implementing one or more of the methods described above. The processor 502 may access the memory 504 by way of a system bus 506. In addition to storing executable instructions, the memory 504 may also store scheduling data for the healthcare worker.

The computing device 500 additionally includes a data store 508 that is accessible by the processor 502 by way of the system bus 506. The data store 508 may include executable instructions, clinical data, scheduling data, etc. The computing device 500 also includes an input interface 510 that allows external devices to communicate with the computing device 500. For instance, the input interface 510 may be used to receive instructions from an external computer device, from a user, etc. The computing device 500 also includes an output interface 512 that interfaces the computing device 500 with one or more external devices. For example, the computing device 500 may display text, images, etc. by way of the output interface 512.

It is contemplated that the external devices that communicate with the computing device 500 via the input interface 510 and the output interface 512 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 500 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 500 may be a distributed system. Thus, for instance, several devices may be in communication by way of a network connection and may collectively perform tasks described as being performed by the computing device 500.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A client computing device executing a client electronic health records application (client EHR) that is in communication with a server electronic health records application (server EHR) executing on a server computing device, wherein the client computing device is configured to display to a healthcare worker, on a display of the client computing device, a graphical user interface (GUI) of the client EHR, wherein the GUI is configured to facilitate generation of schedules that include recurring appointments, the client computing device comprising:
   a processor;
   the display; and
   memory storing the client EHR that, when executed by the processor, causes the processor to perform acts comprising:
      receiving an indication that the healthcare worker has requested to schedule a recurring appointment for a subject;
      responsive to receiving the indication that the healthcare worker has requested to schedule the recurring appointment for the subject, causing the GUI to be displayed on the display of the client computing device, wherein the GUI comprises a matrix of checkboxes that represents a generic month, wherein the matrix of checkboxes comprises:
         five rows of checkboxes, wherein each row of checkboxes represents a different week within the generic month; and
         seven columns of checkboxes, wherein each column of checkboxes represents a different day of a week,
      wherein each checkbox in the matrix of checkboxes is displayed at a different location within the GUI, wherein each checkbox in the matrix of checkboxes is selectable by the healthcare worker;
      receiving a selection of a first checkbox in the matrix of checkboxes, wherein the first checkbox represents an Nth occurrence of a first day within the generic month, wherein N is one of 1, 2, 3, 4, or 5, wherein the first day is one of Sunday, Monday, Tuesday, Wednesday, Thursday, Friday, or Saturday;
      receiving a selection of a second checkbox in the matrix of checkboxes, where the second checkbox represents a Pth occurrence of a second day within the generic month, wherein P is one of 1, 2, 3, 4, or 5, wherein the second day is one of Sunday, Monday, Tuesday, Wednesday, Thursday, Friday, or Saturday; and
      responsive to receiving an indication that the recurring appointment is to be finalized, transmitting scheduling data to the server EHR, wherein the scheduling data comprises an identifier for the first checkbox, an identifier for the second checkbox, and an identifier for the subject, wherein the server EHR updates a computer-implemented schedule for the subject to include the recurring appointment based upon the scheduling data, wherein the recurring appointment occurs during the Nth occurrence of the first day of at least two months and during the Pth occurrence of the second day of the at least two months within the computer-implemented schedule for the subject, and further wherein the computer-implemented schedule is stored in a data store and is updated based upon a search of the data store, the search being based upon the identifier for the subject.

2. The client computing device of claim 1, wherein N is 5.

3. The client computing device of claim 1, wherein the GUI comprises a field that is configured to receive input from the healthcare worker as to a window of time within which the recurring appointment is to recur, and further wherein the computer-implemented schedule is updated based upon the input from the healthcare worker received in the field of the GUI.

4. The client computing device of claim 1, wherein the GUI comprises a field that is configured to receive input from the healthcare worker as to whether the recurring appointment is to recur monthly or bi-monthly, and further wherein the computer-implemented schedule is updated based upon the input from the healthcare worker received in the field of the GUI.

5. The client computing device of claim 1, wherein the matrix of checkboxes consists of 35 checkboxes representing potential days within the generic month.

6. The client computing device of claim 1, wherein the subject is one of a room in a medical facility, the healthcare worker, a second healthcare worker, or a group of healthcare workers.

7. The client computing device of claim 1, wherein the subject is an operating room in a medical facility, wherein the recurring appointment is a scheduled block of time reserved for a surgeon in the operating room, the acts further comprising:
   transmitting a message to the server EHR, wherein the message indicates that the surgeon will not utilize the operating room during at least one of the Nth occurrence of the first day or the Pth occurrence of the second day of the recurring appointment for a given month, wherein the server EHR marks at least one of the Nth occurrence of the first day or the Pth occurrence of the second day in the computer-implemented schedule as available upon receiving the message.

8. A method performed by a client electronic health records application (client EHR) executing on client computing device operated by a healthcare worker, the client EHR is in network communication with a server electronic health records application (server EHR) executing on a server computing device, the method comprising:
   receiving an indication that the healthcare worker has requested to schedule a recurring appointment for a subject;
   responsive to receiving the indication that the healthcare worker has requested to schedule the appointment for the subject, causing a graphical user interface (GUI) of the client EHR to be displayed on a display of the client computing device, wherein the GUI comprises a matrix of checkboxes that represents a generic month, wherein the matrix comprises:
      five rows of checkboxes, wherein each row of checkboxes represents a different week within the generic month; and seven columns of checkboxes, wherein each column of checkboxes represents a different day of a week,
wherein each checkbox in the matrix of checkboxes is displayed at a different location within the GUI, wherein each checkbox in the matrix of checkboxes is selectable by the healthcare worker;
  receiving a selection of a first checkbox in the matrix of checkboxes, wherein the first checkbox represents an Nth occurrence of a first day within the generic month, wherein N is one of 1, 2, 3, 4, or 5, wherein the first day is one of Sunday, Monday, Tuesday, Wednesday, Thursday, Friday, or Saturday;
  receiving a selection of a second checkbox in the matrix of checkboxes, wherein the second checkbox represents a Pth occurrence of a second day within the generic month, wherein P is one of 1, 2, 3, 4, or 5, wherein the second day is one of Sunday, Monday, Tuesday, Wednesday, Thursday, Friday, or Saturday; and
  responsive to receiving an indication that the recurring appointment is to be finalized, transmitting scheduling data to the server EHR, wherein the scheduling data comprises an identifier for the first checkbox, an identifier for the second checkbox, and an identifier for the subject, wherein the server EHR updates the computer-implemented schedule for the subject to include the recurring appointment based upon the scheduling data, wherein the recurring appointment occurs during the Nth occurrence of the first day of at least two months and during the Pth occurrence of the second day of the at least months within the computer-implemented schedule for the subject, and further wherein the computer-implemented schedule is stored in a data store and is updated based upon a search of the data store, the search being based upon the identifier for the subject.

9. The method of claim 8, wherein M is 5.

10. The method of claim 8, wherein the GUI comprises a field that is configured to receive input from the healthcare worker as to a window of time within which the recurring appointment is to recur, and further wherein the computer-implemented schedule is updated based upon the input from the healthcare worker received in the field of the GUI.

11. The method of claim 8, wherein the GUI comprises a field that is configured to receive input from the healthcare worker as to whether the recurring appointment is to recur monthly or bi-monthly, and further wherein the computer-implemented schedule is updated based upon the input from the healthcare worker received in the field of the GUI.

12. The method of claim 8, wherein the matrix of checkboxes consists of 35 checkboxes representing potential days within the generic month.

13. The method of claim 8, wherein the subject is one of a room in a medical facility, the healthcare worker, a second healthcare worker, or a group of healthcare workers.

14. The method of claim 8, wherein the subject is an operating room in a medical facility, wherein the recurring appointment is a scheduled block of time reserved for a surgeon in the operating room, the method further comprising:
  transmitting a message to the server EHR, wherein the message indicates that the surgeon will not utilize the operating room during at least one of the Nth occurrence of the first day or the Pth occurrence of the second day of the recurring appointment for a given month, wherein the server EHR marks at least one of the Nth occurrence of the first day or the Pth occurrence of the second day in the computer-implemented schedule as available upon receiving the message.

15. A non-transitory computer-readable storage medium storing a client electronic health records application (client EHR) that, when executed by a processor of a client computing device being operated by a healthcare worker, causes the processor to perform acts comprising:
  receiving an indication that the healthcare worker has requested to schedule a recurring appointment for a subject;
  responsive to receiving the indication that the healthcare worker has requested to schedule the recurring appointment for the subject, causing a graphical user interface (GUI) of the client EHR to be displayed on the display of the client computing device, wherein the GUI comprises a matrix of checkboxes that represents a generic month, wherein the matrix of checkboxes comprises:
    five rows of checkboxes, wherein each row of checkboxes represents a different week within the generic month; and
    seven columns of checkboxes, wherein each column of checkboxes represents a different day of a week,
  wherein each checkbox in the matrix of checkboxes is displayed at a different location within the GUI, wherein each checkbox in the matrix of checkboxes is selectable by the healthcare worker;
  receiving a selection of a first checkbox in the matrix of checkboxes, wherein the first checkbox represents an Nth occurrence of a first day within the generic month, wherein N is one of 1, 2, 3, 4, or 5, wherein the first day is one of Sunday, Monday, Tuesday, Wednesday, Thursday, Friday, or Saturday;
  receiving a selection of a second checkbox in the matrix of checkboxes, wherein the second checkbox represents a Pth occurrence of a second day within the generic month, wherein P is one of 1, 2, 3, 4, or 5, wherein the second day is one of Sunday, Monday, Tuesday, Wednesday, Thursday, Friday, or Saturday; and
  responsive to receiving an indication that the recurring appointment is to be finalized, transmitting scheduling data to a server electronic health records application (server EHR) that is in network communication with the client EHR, the server EHR executes on a server computing device, wherein the scheduling data comprises an identifier for the first checkbox, an identifier for the second checkbox, and an identifier for the subject, wherein the server EHR updates the computer-implemented schedule for the subject to include the recurring appointment based upon the scheduling data, wherein the recurring appointment occurs during the Nth occurrence of the first day of at least two months and during the Pth occurrence of the second day of the at least two months within the computer-implemented schedule for the subject, and further wherein the computer-implemented schedule is stored in a data store and is updated based upon a search of the data store, the search being based upon the identifier for the subject.

16. The non-transitory computer-readable storage medium of claim 15, wherein N is 5.

17. The non-transitory computer-readable storage medium of claim 15, wherein the GUI comprises a field that is configured to receive input from the healthcare worker as to a window of time within which the recurring appointment is to recur, and further wherein the computer-implemented schedule is updated based upon the input from the healthcare worker received in the field of the GUI.

18. The non-transitory computer-readable storage medium of claim 15, wherein the GUI comprises a field that is configured to receive input from the healthcare worker as to whether the recurring appointment is to recur monthly or bi-monthly, and further wherein the computer-implemented schedule is updated based upon the input from the healthcare worker received in the field of the GUI.

19. The non-transitory computer-readable storage medium of claim 15, wherein the subject is one of a room in a medical facility, the healthcare worker, a second healthcare worker, or a group of healthcare workers.

20. The non-transitory computer-readable storage medium of claim 15, wherein the subject is an operating room in a medical facility, wherein the recurring appointment is a scheduled block of time reserved for a surgeon in the operating room, the acts further comprising:

transmitting a message to the server EHR, wherein the message indicates that the surgeon will not utilize the operating room during at least one of the Nth occurrence of the first day or the Pth occurrence of the second day of the recurring appointment for a given month, wherein the server EHR marks at least one of the Nth occurrence of the first day or the Pth occurrence of the second day in the computer-implemented schedule as available upon receiving the message.

* * * * *